US012778868B2

(12) United States Patent
Ringenbach et al.

(10) Patent No.: US 12,778,868 B2
(45) Date of Patent: Nov. 3, 2026

(54) COSMETIC, DERMATOLOGICAL OR COSMECEUTICAL TREATMENT, IN PARTICULAR PROPIGMENTING

(71) Applicant: Sederma, Le Perray-en-Yvelines (FR)

(72) Inventors: Caroline Ringenbach, Rambouillet (FR); Philippe Mondon, Montrouge (FR)

(73) Assignee: SEDERMA, Le Perray-en-Yvelines (FR)

( * ) Notice: Subject to any disclaimer, the term of this patent is extended or adjusted under 35 U.S.C. 154(b) by 246 days.

(21) Appl. No.: 18/704,339

(22) PCT Filed: Oct. 21, 2022

(86) PCT No.: PCT/EP2022/079399
§ 371 (c)(1),
(2) Date: Apr. 24, 2024

(87) PCT Pub. No.: WO2023/072758
PCT Pub. Date: May 4, 2023

(65) Prior Publication Data

US 2024/0382403 A1 Nov. 21, 2024

(30) Foreign Application Priority Data

Oct. 26, 2021 (FR) ........................................ 2111341

(51) Int. Cl.
*A61K 8/44* (2006.01)
*A61Q 17/04* (2006.01)
*A61Q 19/04* (2006.01)

(52) U.S. Cl.
CPC .............. *A61K 8/445* (2013.01); *A61Q 17/04* (2013.01); *A61Q 19/04* (2013.01); *A61K 2800/78* (2013.01); *A61K 2800/92* (2013.01)

(58) Field of Classification Search
CPC ......... A61K 8/445; A61Q 17/04; A61Q 19/04
See application file for complete search history.

(56) References Cited

U.S. PATENT DOCUMENTS

| | | | | |
|---|---|---|---|---|
| 4,844,884 | A * | 7/1989 | Tur | A61K 8/44 424/59 |
| 5,767,158 | A * | 6/1998 | Suetsugu | A61K 8/41 514/567 |
| 2022/0371989 | A1* | 11/2022 | MacIntyre | A61P 31/04 |

FOREIGN PATENT DOCUMENTS

| | | | |
|---|---|---|---|
| CN | 111514056 | A | 8/2020 |
| FR | 2607699 | A1 | 6/1988 |
| FR | 2702766 | A1 | 9/1994 |
| FR | 3031301 | A1 | 7/2016 |
| WO | 9735842 | A1 | 10/1997 |
| WO | 03017966 | A2 | 3/2003 |
| WO | 2007087956 | A1 | 8/2007 |
| WO | 2014080376 | A2 | 5/2014 |
| WO | 2015181688 | A1 | 12/2015 |
| WO | 2017121445 | A1 | 7/2017 |
| WO | 2019149450 | A1 | 8/2019 |

OTHER PUBLICATIONS

Morsy, R. et al. "Development of hydroxyapatite-chitosan gel sunscreen combating clinical multidrug-resistant bacteria" Journal of Molecular Structure 1143 (2017) 251-258 (Year: 2017).*
International Search Report (PCT/ISA/210) and Written Opinion (PCT/ISA/237) mailed on Jan. 25, 2023, by the European Patent Office as the International Searching Authority for International Application No. PCT/EP2022/079399, 8 pages.

* cited by examiner

*Primary Examiner* — Andrew S Rosenthal
(74) *Attorney, Agent, or Firm* — BUCHANAN INGERSOLL & ROONEY PC

(57) ABSTRACT

According to the invention, at least one tyrosine derivative, in particular N-Palmitoyl-O-methyl-L-Tyrosine, is used for a cosmetic or nutraceutical treatment and/or the manufacture of a cosmetic or nutraceutical composition for improving the general condition of the skin and/or its appendages, in particular for a pro-pigmentation effect.

17 Claims, No Drawings

Specification includes a Sequence Listing.

COSMETIC, DERMATOLOGICAL OR COSMECEUTICAL TREATMENT, IN PARTICULAR PROPIGMENTING

CROSS-REFERENCE TO RELATED APPLICATIONS

This application is the U.S. National Phase of International Application No. PCT/EP2022/079399 filed Oct. 21, 2022, which claims priority to French Application No. 2111341 filed Oct. 26, 2021, the content of each of which is incorporated herein by reference in its entirety.

TECHNICAL FIELD

The present invention relates to a cosmetic, dermatological or cosmeceutical treatment using a tyrosine derivative, in particular a pro-pigmenting topical treatment.

It relates more particularly to a treatment of the skin and its appendages, of human or animal mammals.

It concerns the industries of cosmetic products, dermatological products, and hygiene and personal care products.

«Cosmetic or cosmeceutical treatment» means a treatment which treats healthy skin and/or skin appendages, said treatment being intended to improve or beautify their appearance and condition. Such treatment has no therapeutic purpose.

«Cosmeceutical treatment» (also commonly called nutraceutical) means a non-therapeutic cosmetic treatment by oral route.

BACKGROUND ART

The skin is the first protective barrier between our body and the outside environment. It is also the first image we offer to others. Of all time, skin appearance has been a matter of concern.

The cosmetic and cosmeceutical markets are always seeking for new active ingredients to improve the general condition of the skin and its appendages, in particular to give or restore radiance, moisturise, pigment or depigment them, and protect them against external aggressions, such as UV rays or the cold, calm irritation, redness, acne, reduce micro-oedemas (such as bags under the eyes), reduce dark circles, signs of ageing such as wrinkles and fine lines, restore suppleness and elasticity, treat hair loss, act on adipose tissue, give volume and density, improve texture, etc.

For example, having a tanned complexion gives you a healthy glow and protects DNA in skin cells from UV radiation. But a tan obtained through UV exposure, either naturally from the sun or artificially with a UV lamp, can also cause damages to the skin, immediate (sunburn) and long-term (premature skin ageing due to oxidative stress).

A pro-pigmenting active ingredient acts on synthesis stimulation of melanin, which is the natural pigment of the skin, eyes, body hair, and hair in order to intensify the normal pigmentation of the skin and its appendages without solar or UV radiation. This type of active ingredient represents an alternative to tanning provided by UV exposure.

Body hair includes in particular leg hair, pubic hair, armpit hair, facial hair especially eyebrow, eyelashes, mustache, beard.

For example, the use of the famous molecule dihydroxyacetone (DHA) can be mentioned which, when it comes into contact with the amino acids present on the skin, creates a "tanned" effect. But there are disadvantages to using this molecule, such as the unpleasant smell due to molecules generated by the reaction between DHA and dead skin cells, or the colouring considered too yellow by consumers. Furthermore, it does not provide protection against UV rays because the colouring is not due to a stimulation of the melanin produced in the deep part of epidermis by the melanocytes, but due to a chemical reaction of the upper layer of epidermis.

The cosmetic use of the amino acid tyrosine is also known to accelerate tanning, but free tyrosine is not readily soluble at the necessary and effective concentrations. Other tyrosine-derived tanning agents were subsequently developed, such as TYR-OL™ and TYR-EXCEL™ proposed by Sederma and described respectively in FR2702766 and WO03/017966 based on oleyl tyrosine, whose recommended use is between 0.5 and 1.5% of oleyl tyrosine.

Another method is also used by consumers to get a tanned skin: the use of food supplements often composed of carotenoids and antioxidant vitamins. However, this solution does not provide protection during exposure to UV rays because the pigmentation of the complexion obtained is not due to the synthesis of melanin.

SUMMARY OF THE INVENTION

The present invention aims to provide new cosmetic, dermatological and cosmeceutical treatments for improving or beautifying the general condition of the skin, in particular for artificially pigmenting it when necessary (self-tanning, age spots, pregnancy mask, white spots). The use of these new active ingredients being advantageously possible at lower contents than those of already existing ingredients, while at the same time exhibiting stability over time and good solubility.

For this purpose, the applicant provides the use of at least one compound derived from tyrosine of general formula 1:

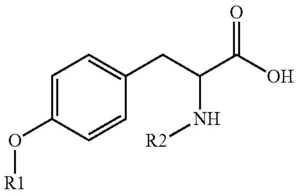

where:

- R1 is a hydrocarbon chain of 1 to 12 carbon atoms; and
- R2 is an acyl or sulfonyl group selected from a biotinoyl group or a group having an alkyl, aryl, aralkyl, alkylaryl, alkoxy, saccharide and aryloxy group, which can be linear, branched, cyclic, polycyclic, unsaturated, hydroxylated, carbonylated, phosphorylated and/or sulfurated, said group having from 1 to 24 carbon atoms, for a non-therapeutic cosmetic or nutraceutical treatment to improve or beautify the general condition of the skin and/or its appendages.

This cosmetic or nutraceutical treatment, particularly suitable for a preventive or curative treatment, and containing at least one compound derived from tyrosine according to the invention, is intended to improve or beautify the general condition of the skin and/or its appendages, in particular adapted to act on:

- skin coloring: for example, by increasing melanin production, attenuating skin spots, and/or homogenising skin complexion; and/or

- hydration: for example, by combating skin dryness and/or protecting or strengthening skin barrier; and/or
- mechanical properties of the skin, for example, firmness, elasticity, suppleness or flaccidity, wrinkles and fine lines: for example, by acting on the synthesis of at least one of the molecules of the dermal extracellular matrix, and/or by limiting the production of free radicals, and/or by limiting the glycation of skin proteins; and/or
- skin problems such as oily and/or acne prone skins: for example by reducing sebum amount and/or by acting on proliferation of bacteria responsible for acne such as *C. acnes*; and/or
- adipose tissue: for example, by acting on lipogenesis and lipolysis; and/or
- signs of skin fatigue, such as dullness, puffiness and/or dark circles: for example, by acting on the production of free radicals, and/or the glycation of skin proteins, and/or the detoxification of cells; and/or
- redness and tightness, for example by calming or soothing skin that has been altered by the cold and/or by UV rays and/or by mechanical friction; and/or
- protection against external aggressions, in particular pollution and radiation: for example, by acting on skin barrier (its renewal and structure) and/or microbiome, by preventing the appearance of micro-inflammations; and/or
- scalp, in particular on anti-dandruff: for example, by acting on scalp dryness and sebum production;
- hair, body hair and nails: for example, by reinforcing their growth and strength by acting on the pilosebaceous unit, re-epithelialization and/or regeneration; and/or Tyrosine derivatives used for the treatment according to the invention may be optically pure consisting of the L or D isomers, or a mixture thereof. Naturally occurring L-isomers are preferred.

Tyrosine derivatives according to the invention may be manufactured by chemical synthesis, or by biotechnological means (fermentation, synthetic biology, etc.).

Preferably according to the invention:

- R1 is a hydrocarbon chain of 1 to 6 carbon atoms; preferably R1 is a methyl or ethyl group; more preferably a methyl group; and/or
- R2 is an acyl or sulfonyl with an alkyl group having from 1 to 24 carbon atoms, which can be linear, branched, saturated or unsaturated, hydroxylated or not, and/or sulfurated; more preferably an acyl with an alkyl group having from 1 to 24 carbon atoms which can be linear or branched; more preferably an acyl with an alkyl group having from 8 to 20 carbon atoms; preferably 14 to 18 carbon atoms.

The group R2 is selected from an octanoyl (C8), decanoyl (C10), lauroyl (C12), myristoyl (C14), palmitoyl (C16), stearoyl (C18), biotinoyl, elaidoyl, oleoyl et lipoyl; more preferably R2 is selected from a myristoyl (C14), palmitoyl (C16), stearoyl (C18); more preferably R2 is a palmitoyl (C16).

Thus, the particularly preferred tyrosine derivative according to the invention is the N-Palmitoyl-O-methyl-L-Tyrosine with R1 group being methyl, R2 group being a palmitoyl (C16), of general formula 2:

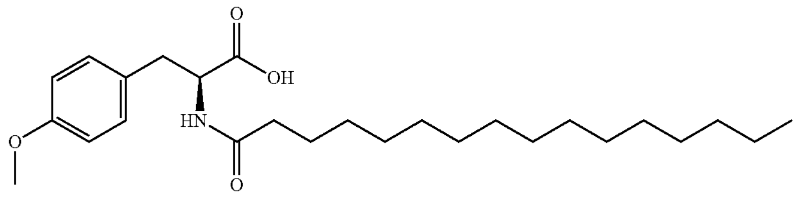

- odors: for example, by having a deodorant action.

The pro-pigmenting cosmetic and/or cosmeceutical treatment according to the invention is more particularly adapted to:

- stimulate skin coloration without UV induction for skin self-tanning; and/or
- prevent and/or treat loss of pigmentation of skin, in particular for preventing and/or treating cutaneous white areas or spots; and/or
- prevent and/or treat loss of pigmentation of hair, body hair, eyelashes and/or eyebrows, in particular to prevent or treat greying, and canities; and/or
- improve skin phototype of a person with white and/or sensitive skin, in particular for preparing the skin and its appendages for sun exposure; and/or
- prevent and/or treat the lack of unification of complexion.

In vitro tests results are given below in the description. They show an effectiveness of the tyrosine derivative according to the invention in pro-pigmentation, and at lower concentrations than the products currently on the market, as well as good solubility. They also show effects in particular on the synthesis of extracellular matrix molecules and inflammation.

Comparative examples are also given to demonstrate the specificity of the derivatization according to the invention.

Preferably according to the invention, the treatment is a topical treatment.

«Topical treatment» or «topical use» means according to the invention, an application that is intended to act where it is applied: skin, mucosa and/or appendages.

The invention provides the use of the tyrosine derivative of the invention as defined above for the manufacture of a cosmetic or nutraceutical composition for a treatment to improve or beautify the general condition of the skin and/or its appendages.

According to the implemented physiologically acceptable medium and the concentration of the tyrosine derivative, this composition may be a concentrated active ingredient for use in a final composition for a consumer, or it may directly constitute said final composition.

"Physiologically acceptable medium" means according to the present invention, without limitation, an aqueous or hydro-alcoholic solution, a water-in-oil emulsion, an oil-in-water emulsion, a micro-emulsion, an aqueous gel, an anhydrous gel, a serum, a dispersion of vesicles, or a powder.

"Physiologically acceptable" means that the compositions are suitable for topical or transdermal use, in contact with mucous membranes, appendages (nails, hair and body hair), scalp and skin of mammals, particularly human, compositions which may be ingested, or injected into the skin, without risk of toxicity, incompatibility, instability, allergic response, and others. This "physiologically acceptable medium" forms what is commonly called the excipient of the composition.

The present invention thus covers a non-therapeutic, cosmetic or nutraceutical topical treatment method for beautifying or improving the appearance and general condition of skin and/or its appendages, and for treating their imperfections, by applying in a subject in need thereof of an effective amount of at least one tyrosine derivative according to the invention or a composition comprising it, in a physiologically acceptable medium.

For the use according to the invention, tyrosine derivative can be solubilized in a physiologically acceptable lipophilic or hydrophilic matrix with, if necessary, a solubilizer, depending on the intended galenic form. Preferably, the physiologically acceptable medium is lipophile, for example containing $C_8$-$C_{10}$ triglycerides.

The at least one tyrosine derivative according to the invention may be associated with one or more other active ingredients at effective concentrations that can act synergistically or additionally for reinforcing and achieving the desired effects described for the invention, such as the following agents: filtering radiations, in particular UVA, UVB, IR or issues from blue light, hydrating, moisturizing, humectant, calming, muscle relaxant, slimming, restructuring, firming, re plumping, lifting, smoothing, acting on blood microcirculation, inflammation, free radicals, anti-aging, anti-fine lines and wrinkles, lightening, acting on complexion, anti-glycation, anti-carbonylation, pro-pigmenting, acting on stratum corneum, on dermal-epidermal junction, on HSP protein production, on firmness, elasticity and tone of skin, on hair growth or anti-regrowth (including eyelashes and eyebrows), on eye contours (dark circles and under eye bags), peptides, vitamins, etc.

More particularly, to improve or beautify the general condition of the skin, the tyrosine derivative according to the invention may be combined, without this list being exhaustive, with one or more active ingredients:

- Moisturising and nourishing, for example Vegesome Moist 24™ (Sederma): active ingredient containing a powder composed of hollow particles of *Lycopodium clavatum* loaded with an extract of *Imperata cylindrica*, which progressively hydrates the epidermis; and/or
- Pigmenting, for example Silverfree™ (Sederma): active ingredient containing the Pal-PP peptide which stimulates several steps of the pigmentation process, and/or the Pal-PA peptide and/or generally the peptides with pro-pigmenting activity described in the applicant's patent application WO2014/080376, and/or TYR-OL™ and TYR-EXCEL™ proposed by Sederma and described in the patents FR 2 702 766 et WO03/017966, based on oleyl tyrosine, and/or one or more of the noreugenin glycoside derivatives described by UNIVERSITY HAMBURG in the patent application WO2017/121445, and/or dihydroxyacetone, and/or one or more derivatives of the chromen-4-one family described by MERCK in the patent application WO2007/087956; and/or the pyrazolin-4,5-dione based compounds described by L'OREAL in the patent application WO97/35842; and/or
- Preventing the signs of photo-aging, for example Venuceane™ (Sederma): active ingredient containing a biotechnological extract of *Thermus thermophilus*, which prevents visible signs of photoaging (spots, wrinkles, dryness . . . ), protects cell structures from UV damage and strengthens skin integrity; and/or
- Skin tensor, for example Feminage™ (Sederma): active ingredient containing an *Engelhardia chrysolepsis* extract, which provides elastic and firming properties to the skin; and/or
- Anti-pollution, for example Citystem™ (Sederma): active ingredient containing a biotechnological extract of *Marrubium vulgare*, which makes the skin soft and smooth, refines the skin texture, reduces the visibility of blackheads while leaving the skin radiant and purified.

Detailed examples are given in the galenic section below.

A composition according to the invention can be applied to the face, body, neckline, scalp, hair, eyelashes, body hair, in any form or vehicle known to those skilled in the art, in particular in the form of a solution, dispersion, emulsion, paste or powder, individually or as a premix or vehicled individually or as a premix in a bound form, incorporated or adsorbed in vectors such as macro-, micro-, or nanocapsules, macro-, micro- or, nanospheres, liposomes, oleosomes or chylomicrons, macro-, micro-, or nanoparticles or macro-, micro or nanosponges, micro- or nanoemulsions, or adsorbed on organic polymer powders, talcs, bentonites, spores or exines, and other inorganic or organic supports.

In cosmetics, applications can be proposed in particular in the ranges of skin care for the face, body, hair and body hair and ranges of make-up treatments, in particular eyelashes and eyebrows.

The composition may be incorporated onto a non-woven or woven material, with natural or synthetic fibers, wool, or any material intended to come into contact with skin and that can be used in clothing, including tights and socks, shorty, day or night underwear, tissues, handkerchiefs or fabric to exert its cosmetic effect via the contact skin/textile and enable continuous topical delivery (cosmetic-textiles).

According to the invention, it is thus also proposed a woven or non-woven fabric comprising at least one a tyrosine derivative, for use in a non-therapeutical cosmetic treatment.

The galenical formulations can enter in different product ranges for personal care and/or beauty products including skin care, cleaning, makeup, cleansing, sunscreen, artificial tanning, pre-shave, shaving or aftershave, moisturizer, humectant, emollient, conditioning, exfoliating, astringent, depilatories or antiperspirant, deodorant, etc.

The Personal Care Products Council ("International cosmetic ingredient dictionary & handbook" published by the "Cosmetic, Toiletry, and Fragrance Association, Inc.", Washington, D.C.) describes a nonlimited wide variety of cosmetic and pharmaceutical ingredients conventionally used in the skin care industry that can be used as additional ingredients in the compositions for the present invention, as long as they are physically and chemically compatible with the other ingredients of the composition and especially with the active ingredients of the present invention. Also, the nature of these additional ingredients should not unacceptably alter the benefits of the active ingredient of the invention. These additional ingredients can be synthetic or natural such as plants extracts or issued from a bio-fermentation process.

Further skin care actives that are particularly useful combined with the composition can be found in Sederma's commercial literature and on the website www.sederma.fr, in Croda's commercial literature and on the website www.croda.fr.

Commercially available actives widely used in cosmetic compositions can also be mentioned as examples: betain, glycerol, Actimoist Bio 2™ (Active organics), Aqua-Cacteen™ (Mibelle AGCosmetics), Aquaphyline™ (Silab), AquaregulK™ (Solabia), Carciline™ (Greentech), Codiavelane™ (Biotech Marine), Dermaflux™ (Arch Chemicals, Inc), Hydra'Flow™ (Sochibo), Hydromoist L™ (Symrise), RenovHyal™ (Soliance), Seamoss™ (Biotech Marine), Essenskin™ (Sederma), Moist 24™ (Sederma), Argireline™ (commercial name of the acetyl hexapeptide-3 from Lipotec), spilanthol or an Acmella oleracea extract known under the trade name Gatuline Expression™, a Boswellia serrata extract known under the trade name Boswellin™, Deepaline PVB™ (Seppic), Syn-AKE™ (Pentapharm), Ameliox™, Bioxilift™ (Silab), PhytoCellTec™Argan (Mibelle), Papilactyl D™ (Silab), Preventhelia™ (Lipotec), or one or more of the following active ingredients sold by Sederma: Subliskin™, Venuceane™, Moist 24™, Vegesome Moist 24™, Essenskin™, Juvinity™, Revidrat™, Resistem™, Chronodyn™, Kombuchka™, Chromocare™, Calmosensine™, Glycokin factor S™, Biobustyl™, Idealift™, Ceramide 2™, Ceramide A2™, Ceramide HO3™, Legance™, Intenslim™, Prodizia™, Beautifeye™, Pacifeel™, Zingerslim™, Meiritage™, Sebuless™, Apiscalp™, Rubistem™, Citystem™, Neonyca™, NG Insaponifiables de Beurre de Karité™, Majestem™, Hydronesis™, Poretect™, Amberstem™, Synchrolife™, Synchrolife™, Sylverfree™, Feminage™, Ameyezing™, Revitalide™, or mixture thereof.

Among plant extracts (in the form of classical plant extracts or prepared by an in vitro process) can be used as additional actives, there may more particularly be mentioned extracts of Ivy, for example English Ivy (*Hedera helix*), of *Bupleurum chinensis*, of *Bupleurum falcatum*, of arnica (*Arnica montana* L.), of rosemary (*Rosmarinus officinalis* N.), of marigold (*Calendula officinalis*), of sage (*Salvia officinalis* L.), of ginseng (*Panax ginseng*), of gingko biloba, of St.-John's-Wort (*Hyperycum perforatum*), of butcher's-broom (*Ruscus aculeatus* L.), of European meadowsweet (*Filipendula ulmaria* L.), of big-flowered Jarva tea (*Orthosiphon stamincus* Benth.), of artichoke (*Cynara scolymus*), of algae (*Fucus vesiculosus*), of birch (*Betula alba*), of green tea, of cola nuts (*Cola nipida*), of horse-chestnut, of bamboo, of *Centella asiatica*, of heather, of fucus, of willow, of mouse-ear, of escine, of cangzhu, of *Chrysanthellum indicum*, of the plants of the *Armeniacea* genus, *Atractylodis platicodon, Sinnomenum, pharbitidis, Flemingia*, de Coleus as *C. forskohlii, C. blumei, C. esquirolii, C. scutellaroides, C. xanthantus* and *C. barbatus*, such as the extract of root of *Coleus barbatus*, extracts of *Ballote*, of *Guioa*, of *Davallia*, of *Terminalia*, of *Barringtonia*, of *Trema*, of *Antirobia, Cecropia, Argania, Dioscoreae* such as *Dioscorea opposita* or Mexican, extracts of *Ammi visnaga*, of *Siegesbeckia*, in particular *Siegesbeckia orientalis*, vegetable extracts of the family of Ericaceae, in particular bilberry extracts (*Vaccinium angustifollium*) or *Arctostaphylos uva ursi, Aloe vera*, plant containing sterols (e.g., phytosterol), Manjistha (extracted from plants of the genus *Rubia*, particularly *Rubia cordifolia*), and Guggal (extracted from plants of the genus *Commiphora*, particularly *Commiphora mukul*), kola extract, chamomile, red clover extract, *Piper methysticum* extract (Kava Kava™ from Sederma), *Bacopa monieri* extract (Bacocalmine™ from Sederma) and sea whip extract, extracts of *Glycyrrhiza glabra*, of mulberry, of *melaleuca* (tea tree), of *Larrea divaricata*, of *Rabdosia rubescens*, of *Euglena gracilis*, of *Fibraurea recisa hirudinea*, of *Chaparral sorghum*, of sun flower, d'*Enantia chlorantha*, of Mitracarpe of *Spermacocea* genus, of *Buchu barosma*, of *Law sonia inermis* L., of *Adiantium capillus-veneris* L., of *Chelidonium majus*, of *Luffa cylindrica*, of "Japanese Mandari" (*Citrus reticulata Blanco* var. *unshiu*), of *Camelia sinensis*, of *Imperata cylindrica*, of *Glaucium Flavum*, of *Cupressus sempervirens*, of *Polygonatum multiflorum*, of *Loveyly hemsleya*, of *Sambucus nigra*, of *Phaseolus lunatus*, of Centaurium, of *Macrocystis pyrifera*, of *Turnera diffusa*, of *Anemarrhena asphodeloides*, of *Portulaca pilosa*, of *Humulus lupulus*, of Coffea arabica, of *Ilex paraguariensis*, or of *Globularia cordifolia*, of *Oxydendron arboretum*, of *Albizzia julibrissin*, of *Zingimber zerumbet smith*, of *Astragalus membranaceus*, of *Atractylodes macrocephalae*, of *Plantago lanceolata*, of *Leontopodium alpinum* (or edelweiss), of *Mirabilis jalapa*, of *Apium graveolens*, of *Marrubium vulgare, Buddleja davidii* Franch, *Syringa vulgaris, Engelhardia chrysolepsis* or orchids.

The compositions of the present invention may include peptides, including, without limitation, di-, tri-, tetra-, penta- and hexapeptides and their derivatives. According to a particular embodiment, the concentration of the additional peptide(s), in the composition, ranges from $1\times10^{-7}$% and 20%, preferably from $1\times10^{-6}$% and 10%, preferably between $1\times10^{-5}$% and 5% by weight.

The term "peptide" refers here to peptides containing 10 amino acids or less, their derivatives, isomers and complexes with other species such as a metal ion e.g., copper, zinc, manganese, magnesium, and others). The term "peptides" refers to both natural peptides and (bio) synthetic peptides. It also refers to compositions that contain peptides and which are found in nature, and/or are commercially available.

Suitable dipeptides for use herein include but are not limited to Carnosine (beta-AH), YR, VW, NF, DF, KT, KC, CK, KP, KK, TT, PA, PM or PP.

Suitable tripeptides for use herein include, but are not limited to RKR, HGG, GHK, GGH, GHG, GKH, KPK, KFK, KavaK, KβAK, KabuK, KacaK, KPK, KMOK, $KMO_2K$ ($MO_2$ being a di-oxygenated sulfoxide methionine), PPL, PPR, SPR, QPA, LPA or SPA.

Suitable non limitative examples of tetrapeptides are KTFK (SEQ ID NO: 1), GQPR (SEQ ID NO: 2), RSRK (SEQ ID NO: 3), KTAK (SEQ ID NO: 4), KAYK (SEQ ID NO: 5), KFYK (SEQ ID NO: 6), or TKPR (SEQ ID NO: 7).

A suitable non limitative example of pentapeptide is KTTKS (SEQ ID NO: 8) and KTSKS (SEQ ID NO: 9) and examples of hexapeptides are GKTTKS (SEQ ID NO: 10) and VGVAPG (SEQ ID NO: 11).

Other suitable peptides for use according to the present invention can be selected, this list being not limitative, from: lipophilic derivatives of peptides, preferably palmitoyl (Pal) derivatives or myristoyl (Myr), and metal complexes as aforementioned (e.g., copper complex of the tripeptide HGG or GHK).

Preferred dipeptides include for example N-Palmitoyl-béta-Ala-His, Pal-KT, le Pal-RT (Sederma).

Preferred tripeptide derivatives include for example the copper derivative of HGG (Lamin™ from Sigma), Pal-GKH and Pal-GHK (from Sederma), Lipospondin (N-Elaidoyl-KFK) and its analogs of conservative substitution, N-Acetyl-RKR-$NH_2$ (Peptide CK+), N-Biot-GHK (from Sederma), Pal-KAvaK, Pal-KβAlaK, Pal-KAbuK, Pal-KAcaK, or Pal-$KMO_2K$ (Matrixyl®synthe'6® from Sederma), Pal-KVK (Syn-Coll™ of DSM), and derivatives thereof.

Mention may also be made here of the anti-aging tripeptides of general formula X-Pro*-Pro*-Xaa-Y described in WO2015181688 Xaa selected from Leu, Arg, Lys, Ala, Ser, and Asp, at the N-terminus, X chosen from H, —CO—$R^1$ and —$SO_2$—$R^1$ and at the C-terminal end Y chosen from OH, $OR^1$, $NH_2$, $NHR^1$ or $NR^1R^2$, $R^1$ and $R^2$ being, independently of one another, chosen from a alkyl, aryl, aralkyl, alkylaryl, alkoxy and aryloxy group, which may be linear, branched, cyclic, polycyclic, unsaturated, hydroxylated, carbonylated, phosphorylated and/or sulfurized, said group possibly possessing in its backbone a heteroatom particularly O, S and/or or N, and Pro* corresponding to Proline, an analogue or derivative thereof; comprising, for example, Myr-PPL-OH and Myr-PPR-OH.

Here can further be cited also the propigmenting and/or pro-mec dipeptides and tripeptides of general Formula X-($Xaa_1$)n-Pro*-$Xaa_2$-Y disclosed in WO2014/080376, with n=0, 1 or 2, $Xaa_1$ an hydrophobic aminoacid selected from Ala, Val, Met, Leu, Iso, Phe, Pro, and analogs and derivatives thereof; or a polar aminoacid selected from Ser, Thr, Tyr, Asp, Glu and analogs and derivatives thereof; and when n=2 the two aminoacids $Xaa_1$ being the same or different; $Xaa_2$ being an hydrophobic aminoacid selected from Ala, Val, Met, Leu, Iso, Phe, and analogs and derivatives thereof, or a basic aminoacid selected from Arg, Lys, His, and analogs and derivatives thereof; at the N terminal end X being selected from H, —CO—$R_1$ and —$SO_2$—$R_1$; at the C terminal end Y being selected from OH, $OR_1$, $NH_2$, $NHR_1$ or $NR_1R_2$; $R_1$ and $R_2$ being, independently from each other, selected from an alkyl, aryl, aralkyl, alkylaryl, alkoxy et aryloxy group, that can be linear, branched, cyclic polycyclic, saturated, unsaturated, hydroxylated, carbonylated, phosphorylated and/or sulfured, said group having or not an O, S and/or N heteroatom in its skeleton and Pro* corresponding to a Proline, analog or derivative thereof; comprising for example the following peptides Pal-SPR-OH, Pal-PPR-OH, Pal-QPA-OH, Pal-LPA-OH, Myr-SPA-OH, Pal-PM-OH, Pal-PA-OH and Pal-PP-OH.

Suitable tetrapeptides derivatives for use as additional peptides according to the present invention include, but are not limited to, Ela-KTAK (SEQ ID NO: 12), Ela-KAYK (SEQ ID NO: 13), Ela-KFYK (SEQ ID NO: 14), Pal-GQPR (SEQ ID NO: 15) or Pal-KTFK (SEQ ID NO: 16).

Suitable pentapeptides derivatives for use as additional peptides herein include, but are not limited to, Pal-KTTKS (SEQ ID NO: 17) (MATRIXYL™, Sederma), Pal-KTSKS (SEQ ID NO: 18), Pal-YGGFXaa (SEQ ID NO: 19) with Xaa being Trp, Phe, Tyr, Tic, 7-hydroxy-Tic or Tpi, or mixtures thereof.

Suitable hexapeptides derivatives for use herein include, but are not limited to, Pal-HLDIIXaa (SEQ ID NO: 20) with Xaa being Trp, Phe, Tyr, Tic, 7-hydroxy-Tic or Tpi, Pal-GKTTKS (SEQ ID NO: 21), Pal-VGVAPG (SEQ ID NO: 22) (DERMAXYL™, Sederma), or mixtures thereof.

The preferred compositions available commercially and sold by Sederma:

- tripeptides or a derivative include Biopeptide-CL™, Maxilip™, or Procapil™ containing GHK;
- tetrapeptides or a derivative include RIGIN™, Eyeliss™ containing Pal-GQPR (SEQ ID NO: 15) and an excipient, Crystalide™ containing Pal-KTFK (SEQ ID NO: 16) vehicle (solvated in microemulsion);
- pentapeptide or a derivative as Matrixyl™ containing Pal-KTTKS (SEQ ID NO: 17).

Can also be mentioned:

- the mixture of Pal-GHK and Pal-GQPR (SEQ ID NO: 15) (Matrixyl™ 3000), and
- the mixture of Pal-GHK and Pal-VGVAPG (SEQ ID NO: 22) (Biobustyl™).

The following marketed peptides can be mentioned as well as additional active ingredients:

- Vialox™ (INCI name=Pentapeptide-3 (synthetic peptide comprising alanine, arginine, isoleucine, glycine and proline)), Syn-ake™ (β-Ala-Pro-Dab-NH-Bzl) or Syn-Coll™ (Pal-Lys-Val-Lys-OH) marketed by Pentapharm;
- Argireline™ (Ac-Glu-Glu-Met-Gln-Arg-Arg-$NH_2$ (INCI name=Acetyl hexapeptide-3) (SEQ ID NO: 23), Leuphasyl™ (Tyr-D-Ala-Gly-Phe-Leu) (SEQ ID NO: 24), Aldenine™ (Gly-His-Lys), Trylagen™ (INCI name=Pseudoalteromonas Ferment Extract, Hydrolyzed Wheat Protein, Hydrolyzed Soy Protein, Tripeptide-10 Citrulline (reaction product of Citrulline and Tripeptide-10 (synthetic peptide constituted of aspartic acid, isoleucine and lysine)), Tripeptide-1), Eyeseryl™ (Ac-β-Ala-His-Ser-His) (SEQ ID NO: 25), Serilesine™ (Ser-Ile-Lys-Val-Ala-Val) (SEQ ID NO: 26) or Decorinyl™ (INCI name: Tripeptide-10 Citrulline=reaction product of Citrulline and Tripeptide-10 (synthetic peptide constituted of aspartic acid, isoleucine and lysine) marketed by Lipotec;
- Collaxyl™ (Gly-Pro-Gln-Gly-Pro-Gln (SEQ ID NO: 27) or Quintescine™ (Cys-Gly) marketed by Vincience;
- Cytokinol™ LS (casein hydrolysate) marketed by Les Laboratoires Serobiologiques/Cognis;
- Kollaren™ (Gly-His-Lys), IP2000™ (Pal-Val-Tyr-Val) or Meliprene™ (INCI name=Monofluoroheptapeptide-1: reaction product of acetic acid and a synthetic peptide comprising arginine, glycine, glutamic acid, histidine, norleucine, p-fluorophenylalanine and tryptophan) marketed by l'Institut Européen de Biologie Cellulaire;
- Neutrazen™ (Pal-His-D-Phe-Arg-$NH_2$) marketed by Innovations; or
- BONT-L-Peptide™ (INCI name=Palmitoyl Hexapeptide-19: reaction product of palmitic acid and Hexapeptide-19 (synthetic peptide constituted of asparagine, aspartic acid, lysine and methionine), Timp-Peptide™ (INCI name=Acetyl Hexapeptide-20: reaction product obtained by acetylation of Hexapeptide-20 (synthetic peptide constituted of alanine, glycine, lysine, valine and proline) or ECM Moduline™ (INCI name=Palmitoyl Tripeptide-28: reaction product of palmitic acid and Tripeptide-28 (synthetic peptide constituted of arginine, lysine and phenylalanine) marketed by Infinitec Activos.

It is also possible to envisage combining the invention with one or more cyclic peptides, in particular those extracted from linseed oil described in the Applicant's patent application FR1850845.

Tyrosine derivatives according to the invention or composition containing it can be preferentially combined with at least one compound chosen among vitamin B3, compounds as niacinamide or tocopherol, retinoids compounds as retinol, hexamidine, α-lipoic acid, resveratrol or DHEA, hyaluronic acid, peptides, in particular N-acetyl-Tyr-Arg-O-hexadecyl, Pal-VGVAPG (SEQ ID NO: 20), Pal-KTTKS (SEQ ID NO: 16), Pal-KTSKS (SEQ IS NO: 18), Pal-GHK, Pal-$KMO_2K$, Pal-GQPR (SEQ ID NO: 14) and Pal-K(P)HG (MATRIXYL™ Morphomics™, Sederma) that are classic active agents used in topical cosmetic or dermo-pharmaceutical compositions.

Tyrosine derivatives or the composition according to the invention can be applied locally to the targeted areas.

The effective amount of tyrosine derivatives according to the invention, that is to say its dosage, depends on the destination of the composition. It depends on various factors, such as the age, the condition of the patient, the severity of the disorder or disease and the administration mode. An effective amount means a non-toxic amount enough to achieve the desired effect.

In a cosmetic composition according to the invention containing at least one a tyrosine derivative, to be present in an effective amount, is generally present in an amount ranging from 0.000001% (0.01 ppm) and 15% (150 000 ppm) based on the total weight of the composition, preferably ranging from 0.00001% (0.1 ppm) and 10% (100 000 ppm), depending on the destination of the composition and the more or less pronounced desired effect. More preferably, the effective amount is between 0.0001% (1 ppm) and 0.01% (100 ppm) based on the total weight of the composition, which is much lower than current market standards.

All percentages and ratios used herein are by weight of the total composition and all measurements are made at 25° C. unless it is otherwise specified.

For indication, for a cosmetic face treatment, the European standard dosage of a cream is 2.72 $mg/cm^2$/day/person and for a cosmetic body treatment the European standard dosage of a lotion is 0.5 $mg/cm^2$/day/person.

According to other features, the cosmetic treatment method according to the invention can be combined with one or more other treatment methods targeting the skin such as luminotherapy, heat or aromatherapy treatments.

It is possible to offer devices with several compartments or kits may be proposed to apply the method described above which may include for example and non-restrictively, a first compartment containing a composition comprising the tyrosine derivative of the invention, and in a second compartment a second tyrosine derivative of the invention in an excipient and/or an additional active ingredient, the compositions contained in the said first and second compartments in this case being considered to be a combination composition for simultaneous, separate or stepwise use in time, particularly in one of the treatment methods recited above.

DETAILED DESCRIPTION

The present invention will be better understood in the light of the following description of an embodiment and in vitro tests.

1) Composition Preparation for Implementing the Present Invention a) Example of Obtaining a Preferred Tyrosine Derivative for the Implementation of the Invention: N-Palmitoyl-O-methyl-L-Tyrosine The tyrosine derivative is prepared by chemical synthesis. The starting material is methylated L-tyrosine (H-Tyr(Me)-OH) which is commercially available, and which is suspended in a suitable solvent (N-Butyl-Pyrolidone), then heated and palmitoyl chloride is added. The obtained solid is filtered and then dissolved in a mixture of solvents to crystallize. The crystallized product is then washed with a suitable solvent and dried.

b) Example of Preparation of a Cosmetic Composition According to the Invention who is an Active Ingredient Comprising the Tyrosine Derivative The tyrosine derivative is lipophilic. It is solubilised, for example at 2000 ppm, in a $C_8C_{10}$ triglyceride matrix.

2) In Vitro Tests

They were conducted on the tyrosine derivative N-Palmitoyl-O-methyl-L-Tyrosine produced as described above. The in vitro tests below were carried out on normal human melanocytes (NHM), mouse B16 cells, keratinocytes or fibroblasts, depending on the tests. The tyrosine derivative according to the invention was tested in solution in a solvent (acidified dimethylsulfoxide (DMSO)), at concentrations recommended for in vitro use.

a) Melanin Stimulation Without UV Induction

Protocol

NHM are cultivated and placed in contact with the product according to the invention for 10 days. At the end of this contact period, the mats are ground and the melanin is extracted from the cells. The quantity of melanin is assessed by spectrophotometry, using a standard range established previously from a melanin solution and compared to the control. A protein assay using the bicinchoninic acid (BCA) method is performed to estimate the quantity of cells and to standardise the obtained data.

B16 mouse pigment cells are cultivated and placed in contact with the product according to the invention for 2 days. For this type of cells, tyrosinase is also assayed. Tyrosinase is the first enzyme in the chain of melanogenesis, changing tyrosine to DOPA-quinone.

Results

The number of cells did not change significantly, the product being neither toxic nor multiplication activator.

TABLE 1

Effect of the tyrosine derivative according to the invention on melanin production by NHM (n = 4):

| | Melanin ($\mu g/mL/10^6$ cell.) | Variation (%); Significance |
|---|---|---|
| Control | 269 +/− 19 | Reference |
| 5.5 ppm of the tyrosine derivative according to the invention | 404 +/− 42 | +50%; $p < 0.01$ |
| 11 ppm of the tyrosine derivative according to the invention | 501 +/− 41 | +86%; $p < 0.01$ |

These results show that the melanin production by NHM is significantly increased by the tyrosine derivative according to the invention without UV induction.

TABLE 2

Effect of tyrosine derivative according to the invention on the melanin production and tyrosinase activity by B16 mouse pigment cells (n = 4):

| | Melanin (μg/mL/$10^6$ cell.) | Variation (%); Significance | Tyrosinase (U/1000 μg protein) | Variation (%); Significance |
|---|---|---|---|---|
| Control | 136 +/− 2.8 | Reference | 2.5 +/− 0 | Reference |
| 5.5 ppm of the tyrosine derivative according to the invention | 171.1 +/− 2.3 | +26%; p < 0.01 | 2.8 +/− 0 | +9.7%; p < 0.01 |
| 11 ppm of the tyrosine derivative according to the invention | 220.7 +/− 8.7 | +62%; p < 0.01 | 3.1 +/− 0 | +20.5%; p < 0.01 |

These results show that the melanin production and tyrosinase activity by B16 mouse cells are significantly increased by the tyrosine derivative according to the invention without UV induction.

Both tests, on NHM and B16 cells, demonstrate the pro-pigmenting activity of the tyrosine derivative according to the invention, and the cosmetic or cosmeceutical use that may result.

b) Increase of Keratinocytes Phagocytosis

Protocol

Normal human keratinocytes (NHK) are seeded and cultured and, once at 50% sub-confluence, receive the tyrosine derivative according to the invention, or its solvent, at different concentrations for 24 h. At the end of this period, the cells receive the fluorescent microbeads mimicking melanosomes for 3 h. Then, the cells are rinsed to remove excess beads, and the mats are visualized under a fluorescence microscope to quantify phagocytosis. The cell concentration is estimated using the Hoescht method.

Results

TABLE 3

Effect of tyrosine derivative according to the invention on NHK phagocytosis (n = 4):

| | Phagocytosis (μbeas: (Total Area/1000)) | Variation (%); Significance |
|---|---|---|
| Control | 3864 +/− 582 | Reference |
| 5.5 ppm of the tyrosine derivative according to the invention | 6599 +/− 1115 | +71%; p < 0.01 |
| 11 ppm of the tyrosine derivative according to the invention | 9910 +/− 1161 | +129%; p < 0.01 |

These results show that the NHK phagocytosis is significantly increased by the tyrosine derivative according to the invention.

This demonstrates that more melanin is transferred to the keratinocytes, which further increases the coloring of the skin and better protects the cells from solar irradiation.

d) Synthesis of the Extracellular Matrix of Keratinocytes

Protocol

HaCaT keratinoctes are seeded and cultured and, once at sub-confluence, receive the tyrosine derivative according to the invention, or its solvent, at different concentrations for 3 days. At the end of this period, the media are collected for hyaluronic acid and laminin assays using ELISA methods. The cell concentration is estimated using the Hoescht method.

Results

TABLE 4

Effect of tyrosine derivative according to the invention on hyaluronic acid production (n = 4):

| | Hyaluronic acid (ng/$10^6$ cell.) | Variation (%); Significance |
|---|---|---|
| Control | 298 +/− 21 | Reference |
| 1.375 ppm of the tyrosine derivative according to the invention | 402 +/− 35 | +35%; p < 0.01 |
| 2.75 ppm of the tyrosine derivative according to the invention | 391 +/− 25 | +31%; p < 0.01 |

These results show that hyaluronic acid in keratinocytes is significantly increased by the tyrosine derivative according to the invention.

This shows, in particular, that skin hydration and elasticity are improved with the use of the tyrosine derivative according to the invention.

TABLE 5

Effect of tyrosine derivative according to the invention on laminin production (n = 4):

| | Laminin (ng/$10^6$ cell.) | Variation (%); Significance |
|---|---|---|
| Control | 66 +/− 5 | Reference |
| 2.75 ppm of the tyrosine derivative according to the invention | 88 +/− 3 | +33%; p < 0.01 |
| 5.5 ppm of the tyrosine derivative according to the invention | 111 +/− 9 | +69%; p < 0.01 |

Laminins are molecules found in the epidermis that are involved in strengthening the dermis/epidermis junction. They are contained in the basal layer and participate in the anchoring of the cell surfaces to the basal lamina. They ensure to the keratinocytes of the basal layer to be better anchored and help to maintain the suppleness of the epidermis.

These results show that laminins in keratinocytes are significantly increased by the tyrosine derivative according to the invention.

e) Anti-Inflammatory Activity

Protocol

Keratinocytes are seeded and cultured and, once at sub-confluence, receive the tyrosine derivative according to the invention, or its solvent, at different concentrations. After 24 hours, the cells are rinsed and then exposed to UVB, and the cells are then re-treated with the media containing the tyrosine derivative according to the invention at different concentrations for 24 hours. Other cases are not exposed. The culture media are assayed for PGE2, IL6 and IL8 using ELISA methods. The number of cells was estimated using the Hoescht method.

The same protocol is applied in parallel to Fibroblasts.

Results

TABLE 6

Effect of the tyrosine derivative according to the invention on PGE2 contained in keratinocytes (n = 3):

| | PGE2 without irradiation (ng/$10^6$ cell.) | Variation (%); Significance | PGE2 with UVB irradiation (ng/$10^6$ cell.) | Variation (%); Significance |
|---|---|---|---|---|
| Control | 129 +/− 5 | Reference | 268 +/− 20 | Reference |
| 5.5 ppm of the tyrosine derivative according to the invention | 51 +/− 5 | −60%; $p < 0.01$ | 101 +/− 7 | −62%; $p < 0.01$ |
| 11 ppm of the tyrosine derivative according to the invention | 54 +/− 5 | −58%; $p < 0.01$ | 72 +/− 3 | −73%; $p < 0.01$ |

These results show that PGE2 in keratinocytes induced by UVB irradiation or not irradiated, is significantly decreased by the tyrosine derivative according to the invention.

TABLE 7

Effect of the tyrosine derivative according to the invention on PGE2 contained in fibroblasts (n = 3):

| | PGE2 without irradiation (ng/$10^6$ cell.) | Variation (%); Significance | PGE2 with UVB irradiation (ng/$10^6$ cell.) | Variation (%); Significance |
|---|---|---|---|---|
| Control | 11073 +/− 1110 | Reference | 9067 +/− 549 | Reference |
| 5.5 ppm of the tyrosine derivative according to the invention | 7420 +/− 422 | −32%; $p < 0.01$ | 7332 +/− 478 | −19%; nsd* |
| 11 ppm of the tyrosine derivative according to the invention | 6470 +/− 311 | −41%; $p < 0.01$ | 6117 +/− 735 | −33%; $p < 0.01$ |

*nsd: non significant data

These results show that PGE2 in fibroblasts induced by UVB irradiation, is significantly decreased by tyrosine derivative according to then invention.

TABLE 8

Effect of the tyrosine derivative according to the invention on IL6 et IL8 contained in keratinocytes (n = 2):

| | IL6 with UVB irradiation (ng/$10^6$ cell.) | Variation (%); Significance | IL8 with UVB irradiation (ng/$10^6$ cell.) | Variation (%); Significance |
|---|---|---|---|---|
| Control | 7.4+/−0.7 | Reference | 1555+/−142 | Reference |
| 5.5 ppm of tyrosine derivative according to the invention | 4.3 +/− 0.7 | −42%; $p < 0.01$ | 880 +/− 142 | −43%; $p < 0.01$ |
| 11 ppm of tyrosine derivative according to the invention | 0.7 +/− 0 | −90%; $p < 0.01$ | 853 +/− 115 | −45%; $p < 0.01$ |

These results show that IL6 and IL8 in keratinocytes induced by UVB irradiation or not irradiated, is significantly decreased by the tyrosine derivative according to the invention.

These results show an anti-inflammatory preventive effect of the tyrosine derivative according to the invention. The cells are better protected. From a cosmetic point of view, the treatment according to the invention prevents discomforts, such as tightness, and unsightliness, such as micro-redness of the skin, for example due to external aggressions such as pollution, radiation or cold.

f) Comparative Tests

Test 1: Comparison of Oleyl Tyrosine vs. the Tyrosine Derivative According to the Invention Protocol The tests were carried out on NHM, the protocol being the same to the one above of point a)

Results

At 16 ppm, the tyrosine derivative according to the invention induces an increase in pigmentation of these cells of 52% ($p<0.01$ vs. control) whereas 16 ppm of oleyl tyrosine induces a 9% change (nsd vs. control). With approximately 3 times more oleyl tyrosine applied to the cells, a +35% increase in NHM pigmentation is achieved ($p<0.01$ vs. control).

At equivalent concentration, the tyrosine derivative according to the invention is more active than oleyl tyrosine. About 3 times more oleyl tyrosine is needed to have an equivalent effect compared to the tyrosine derivative according to the invention.

N-Palmitoyl-L-Tyrosine have R1=H whereas for the tyrosine derivative according to the invention have R1=$CH_3$, $CH_3$ being a hydrocarbon chain of 1 carbon atom.

Test 2: On NHM With Assessment by Spectrophotometry

Protocol

The protocol is the same as that of point a) above.

Results

These results show that the tyrosine derivative according to the invention produces more melanin than N-Palmitoyl-L-Tyrosine.

TABLE 9

Effect of tyrosine derivative according to the invention on melanin production by NHM (n = 4):

| | Variation (%); Significance | |
|---|---|---|
| | N-Palmitoyl-L-Tyrosine | N-Palmitoyl-O-methyl-L-Tyrosine |
| Control | Reference | Reference |
| 12.5 μM of the tyrosine derivative: 5.5 ppm of N-Palmitoyl-O-methyl-L-Tyrosine 5.25 ppm of N-Palmitoyl-L-Tyrosine | +7%; dns | +50%; $p < 0.01$ |
| 25 μM of the tyrosine derivative: 11 ppm of N-Palmitoyl-O-methyl-L-Tyrosine 10.5 ppm of N-Palmitoyl-L-Tyrosine | +10%; dns | +86%; $p < 0.01$ |

Test 3: on NHM with Assessment by Microscopic Observation by Expert

Protocol

NHM are cultivated and placed in contact with the product according to the invention for 10 days. At the end of this contact period, cells are observed with a microscope and variation of pigmentation of cells versus control is evaluated by an expert.

Results

TABLE 10

Variation of pigmentation of cells versus control:

| | N-Palmitoyl-L-Tyrosine | N-Palmitoyl-O-methyl-L-Tyrosine |
|---|---|---|
| 12.5 μM of the tyrosine derivative: 5.5 ppm of N-Palmitoyl-O-methyl-L-Tyrosine 5.25 ppm of N-Palmitoyl-L-Tyrosine | 0 | + |
| 25 μM of the tyrosine derivative: 11 ppm of N-Palmitoyl-O-methyl-L-Tyrosine 10.5 ppm of N-Palmitoyl-L-Tyrosine | 0 | ++ |

Visually, only N-Palmitoyl-O-methyl-L-Tyrosine presents a pro-pigmenting effect on human melanocytes.

Conclusion

Both tests show that the derivative of Tyrosine according to the invention, having a derivatization on the R1 position, has a propigmentation effect, whereas the Tyrosine derivative having no derivatization on the R1 position has no effect.

3) Galenic

Examples of galenic formulation are given below containing at least one compound derived from tyrosine according to the invention as active molecule, in particular as formulated in the active ingredient described in point 1) b) above.

Moreover, this formulation may also contain other additional cosmetic active ingredients, the latter possibly supporting and/or complementing the activity of the active ingredient according to the invention. These ingredients may be of any category depending on their function(s), the place of application (body, face, neck, bust, hands, etc.), the desired final effect and the targeted consumer, for example anti-ageing, moisturising, firming, anti-redness, anti-stretch marks, etc.

To be effective, the recommended use concentration of the tyrosine derivative according to the invention is between 0.002% and 0.01% with regard to the total weight of the composition to have an effective concentration. By comparison, the recommended use of oleyl tyrosine is between 0.5 and 1.5%.

Example 1: Self-Tanning Cream

TABLE 11

| Raw material | % | INCI Name |
|---|---|---|
| Part A | | |
| Span 60™ (Croda) | 3.00 | Sorbitan Stearate |
| Cyclopentasiloxane (and) Cyclohexasiloxane | 2.00 | Cyclopentasiloxane (and) Cyclohexasiloxane |
| Crodamol OP™ (Croda) | 3.00 | Ethylhexyl Palmitate |
| Arlacel 170™ (Croda) | 3.00 | Glyceryl Stearate (and) PEG-100 Stearate |
| Ethylhexyl Methoxycinnamate | 1.00 | Ethylhexyl Methoxycinnamate |
| Ethylhexyl Dimethyl PABA | 1.00 | Ethylhexyl Dimethyl PABA |
| Part B | | |
| $H_2O$ | qsp | Water |
| Carbomer | 0.40 | Carbomer |
| Part C | | |
| Glycerin | 5.00 | Glycerin |
| Preservatives | qs | — |
| Part D | | |
| Active ingredient containing the tyrosine derivative according to the invention | 2.00 | |
| Part E | | |
| Osmocide™ 2 (Sederma) | 4.00 | Glycerine (and) Water (and) PEG-8 (and) Caprylyl Glycol (and) Sodium Polyacrylate |
| Part F | | |
| Potassium sorbate | 0.10 | Potassium sorbate |
| Part G | | |
| $H_2O$ | 6.00 | Water |
| Sodium hydroxide at 30% | 0.60 | Sodium hydroxide |

Protocol

Heat A. Weigh B and leave to stand. Melt C, then add B. Heat B+C, then add A, then D, then E, then F and finally G. Blend.

Example 2: Oil Spray for Homogenizing the Complexion

TABLE 12

| Raw material | % | INCI Name |
|---|---|---|
| Part A | | |
| Crodamol™ GTCC (Croda) | qsp | Caprylic/Capric Triglyceride |
| Crodamol™ OS (Croda) | 20.00 | Ethylhexyl Stearate |
| Ethylhexyl Methoxycinnamate | 2.00 | Ethylhexyl Methoxycinnamate |

TABLE 12-continued

| Raw material | % | INCI Name |
|---|---|---|
| Ethylhexyl Dimethyl PABA | 2.00 | Ethylhexyl Dimethyl PABA |
| Tocopherol acetate | 0.20 | Tocopherol acetate |
| Part B | | |
| Active ingredient containing the tyrosine derivative according to the invention | 2.00 | |

Protocol

Blend A, then add B, then add C. Blend.

Example 3: Skin Radiance Gel

TABLE 13

| Raw material | % | INCI Name |
|---|---|---|
| Part A | | |
| $H_2O$ | qsp | Water |
| Carbomer | 0.20 | Carbomer |
| Part B | | |
| PEG 400 | 5.00 | PEG 400 |
| Preservatives | Qs | — |
| Part C | | |
| Dimethicone | 4.00 | Dimethicone |
| Acrylates/C10-30 Alkyl Acrylate Cross Polymer | 0.20 | Acrylates/C10-30 Alkyl Acrylate Cross Polymer |
| Part D | | |
| Tween 20™ (Croda) | 1.00 | Polysorbate 20 |
| Active ingredient containing the tyrosine derivative according to the invention | 2.00 | |
| Part E | | |
| Potassium sorbate | 0.10 | Potassium sorbate |
| Part F | | |
| Osmocide™ 2 (Sederma) | 4.00 | Glycerine (and) Water (and) PEG-8 (and) Caprylyl Glycol (and) Sodium Polyacrylate |
| Part G | | |
| $H_2O$ | 5.00 | Water |
| Sodium hydroxide | 0.60 | Sodium hydroxide |

Protocol

Heat part B. Mix A+B and C+D separately. Add (C+D) to (A+B), then E, then F. Leave to stand and add G, then H.

Examples of ingredients that can be added to these formulations (marketed by SEDERMA):

VENUCEANE™: active ingredient containing a biotechnological extract of *Thermus thermophilus*, which prevents visible signs of photoaging (spots, wrinkles, dryness . . . ), protects cellular structures from UV damage and strengthens skin integrity; AQUALANCE™: hydrating osmoprotective active ingredient; CALMOSENSINE™: calming active ingredient.

SEQUENCE LISTING

```
Sequence total quantity: 27
SEQ ID NO: 1            moltype = AA  length = 4
FEATURE                 Location/Qualifiers
REGION                  1..4
                        note = ARTIFICIAL SEQUENCE
source                  1..4
                        mol_type = protein
                        organism = synthetic construct
SEQUENCE: 1
KTFK                                                                 4

SEQ ID NO: 2            moltype = AA  length = 4
FEATURE                 Location/Qualifiers
REGION                  1..4
                        note = synthetic peptide
source                  1..4
                        mol_type = protein
                        organism = synthetic construct
SEQUENCE: 2
GQPR                                                                 4

SEQ ID NO: 3            moltype = AA  length = 4
FEATURE                 Location/Qualifiers
REGION                  1..4
                        note = synthetic peptide
source                  1..4
                        mol_type = protein
                        organism = synthetic construct
SEQUENCE: 3
RSRK                                                                 4

SEQ ID NO: 4            moltype = AA  length = 4
FEATURE                 Location/Qualifiers
REGION                  1..4
                        note = Synthetic peptide
source                  1..4
                        mol_type = protein
                        organism = synthetic construct
SEQUENCE: 4
KTAK                                                                 4

SEQ ID NO: 5            moltype = AA  length = 4
FEATURE                 Location/Qualifiers
REGION                  1..4
                        note = Synthetic peptide
source                  1..4
                        mol_type = protein
                        organism = synthetic construct
SEQUENCE: 5
KAYK                                                                 4

SEQ ID NO: 6            moltype = AA  length = 4
FEATURE                 Location/Qualifiers
REGION                  1..4
                        note = Synthetic peptide
source                  1..4
                        mol_type = protein
                        organism = synthetic construct
SEQUENCE: 6
KFYK                                                                 4

SEQ ID NO: 7            moltype = AA  length = 4
FEATURE                 Location/Qualifiers
REGION                  1..4
                        note = Artificial sequence
source                  1..4
                        mol_type = protein
                        organism = synthetic construct
SEQUENCE: 7
TKPR                                                                 4

SEQ ID NO: 8            moltype = AA  length = 5
FEATURE                 Location/Qualifiers
REGION                  1..5
                        note = synthetic peptide
source                  1..5
                        mol_type = protein
                        organism = synthetic construct
```

-continued

```
SEQUENCE: 8
KTTKS                                                              5

SEQ ID NO: 9              moltype = AA  length = 5
FEATURE                   Location/Qualifiers
REGION                    1..5
                          note = synthetic peptide
source                    1..5
                          mol_type = protein
                          organism = synthetic construct
SEQUENCE: 9
KTSKS                                                              5

SEQ ID NO: 10             moltype = AA  length = 6
FEATURE                   Location/Qualifiers
REGION                    1..6
                          note = Synthetic peptide
source                    1..6
                          mol_type = protein
                          organism = synthetic construct
SEQUENCE: 10
GKTTKS                                                             6

SEQ ID NO: 11             moltype = AA  length = 6
FEATURE                   Location/Qualifiers
REGION                    1..6
                          note = synthetic peptide
source                    1..6
                          mol_type = protein
                          organism = synthetic construct
SEQUENCE: 11
VGVAPG                                                             6

SEQ ID NO: 12             moltype = AA  length = 4
FEATURE                   Location/Qualifiers
REGION                    1..4
                          note = Synthetic peptide
MOD_RES                   1
                          note = amidation by a Elaidoyl chain on the N terminal end
source                    1..4
                          mol_type = protein
                          organism = synthetic construct
SEQUENCE: 12
KTAK                                                               4

SEQ ID NO: 13             moltype = AA  length = 4
FEATURE                   Location/Qualifiers
REGION                    1..4
                          note = Synthetic peptide
MOD_RES                   1
                          note = amidation by a Elaidoyl chain on the N terminal end
source                    1..4
                          mol_type = protein
                          organism = synthetic construct
SEQUENCE: 13
KAYK                                                               4

SEQ ID NO: 14             moltype = AA  length = 4
FEATURE                   Location/Qualifiers
REGION                    1..4
                          note = Synthetic peptide
MOD_RES                   1
                          note = amidation by a Elaidoyl chain on the N terminal end
source                    1..4
                          mol_type = protein
                          organism = synthetic construct
SEQUENCE: 14
KFYK                                                               4

SEQ ID NO: 15             moltype = AA  length = 4
FEATURE                   Location/Qualifiers
REGION                    1..4
                          note = synthetic peptide
MOD_RES                   1
                          note = amidation by a Palmitoyl chain on the N terminal end
source                    1..4
                          mol_type = protein
                          organism = synthetic construct
SEQUENCE: 15
```

-continued

```
GQPR                                                          4

SEQ ID NO: 16          moltype = AA  length = 4
FEATURE                Location/Qualifiers
REGION                 1..4
                       note = ARTIFICIAL SEQUENCE
MOD_RES                1
                       note = amidation by a Palmitoyl chain on the N terminal end
source                 1..4
                       mol_type = protein
                       organism = synthetic construct
SEQUENCE: 16
KTFK                                                          4

SEQ ID NO: 17          moltype = AA  length = 5
FEATURE                Location/Qualifiers
REGION                 1..5
                       note = synthetic peptide
MOD_RES                1
                       note = amidation by a Palmitoyl chain on the N terminal end
source                 1..5
                       mol_type = protein
                       organism = synthetic construct
SEQUENCE: 17
KTTKS                                                         5

SEQ ID NO: 18          moltype = AA  length = 5
FEATURE                Location/Qualifiers
REGION                 1..5
                       note = synthetic peptide
MOD_RES                1
                       note = amidation by a Palmitoyl chain on the N terminal end
source                 1..5
                       mol_type = protein
                       organism = synthetic construct
SEQUENCE: 18
KTSKS                                                         5

SEQ ID NO: 19          moltype = AA  length = 5
FEATURE                Location/Qualifiers
REGION                 1..5
                       note = synthetic peptide
MOD_RES                1
                       note = amidation by a Palmitoyl chain on the N terminal end
SITE                   5
                       note = MISC_FEATURE - Xaa being either a Proline P or a
                        Leucine L.
source                 1..5
                       mol_type = protein
                       organism = synthetic construct
SEQUENCE: 19
YGGFX                                                         5

SEQ ID NO: 20          moltype = AA  length = 6
FEATURE                Location/Qualifiers
REGION                 1..6
                       note = Synthetic peptide
MOD_RES                1
                       note = amidation by a Palmitoyl chain on the N terminal end
SITE                   6
                       note = MISC_FEATURE - Xaa being Trp, Phe, Tyr, Tic,
                        7-hydroxy-Tic or Tpi
source                 1..6
                       mol_type = protein
                       organism = synthetic construct
SEQUENCE: 20
HLDIIX                                                        6

SEQ ID NO: 21          moltype = AA  length = 6
FEATURE                Location/Qualifiers
REGION                 1..6
                       note = synthetic peptide
```

-continued

```
MOD_RES                 1
                        note = amidation by a Palmitoyl chain on the N terminal end
source                  1..6
                        mol_type = protein
                        organism = synthetic construct
SEQUENCE: 21
GKTTKS                                                                       6

SEQ ID NO: 22           moltype = AA  length = 6
FEATURE                 Location/Qualifiers
REGION                  1..6
                        note = synthetic peptide
MOD_RES                 1
                        note = amidation by a Palmitoyl chain on the N terminal end
source                  1..6
                        mol_type = protein
                        organism = synthetic construct
SEQUENCE: 22
VGVAPG                                                                       6

SEQ ID NO: 23           moltype = AA  length = 6
FEATURE                 Location/Qualifiers
REGION                  1..6
                        note = synthetic peptide
MOD_RES                 1
                        note = Acetylation on the N-terminal end
source                  1..6
                        mol_type = protein
                        organism = synthetic construct
SEQUENCE: 23
EEMQRR                                                                       6

SEQ ID NO: 24           moltype = AA  length = 5
FEATURE                 Location/Qualifiers
REGION                  1..5
                        note = synthetic peptide
source                  1..5
                        mol_type = protein
                        organism = synthetic construct
SEQUENCE: 24
YAGFL                                                                        5

SEQ ID NO: 25           moltype = AA  length = 4
FEATURE                 Location/Qualifiers
REGION                  1..4
                        note = synthetic peptide
source                  1..4
                        mol_type = protein
                        organism = synthetic construct
SEQUENCE: 25
AHSH                                                                         4

SEQ ID NO: 26           moltype = AA  length = 6
FEATURE                 Location/Qualifiers
REGION                  1..6
                        note = synthetic peptide
source                  1..6
                        mol_type = protein
                        organism = synthetic construct
SEQUENCE: 26
SIKVAV                                                                       6

SEQ ID NO: 27           moltype = AA  length = 6
FEATURE                 Location/Qualifiers
REGION                  1..6
                        note = synthetic peptide
source                  1..6
                        mol_type = protein
                        organism = synthetic construct
SEQUENCE: 27
GPQGPQ                                                                       6
```

The invention claimed is:

1. A non-therapeutic cosmetic or nutraceutical method to improve or beautify the general condition of skin and/or its appendages, comprising contacting the skin and/or its appendages with at least one compound derived from tyrosine of general formula 1:

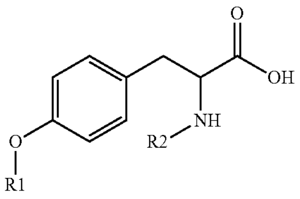

wherein:

R1 is a hydrocarbon chain of 1 to 12 carbon atoms; and

R2 is selected from octanoyl (C8), decanoyl (C10), lauroyl (C12), myristoyl (C14), palmitoyl (C16), stearoyl (C18), biotinoyl, elaidoyl, oleoyl and lipoyl, and wherein the method is a self-tanning treatment to stimulate skin coloring without UV induction.

2. A cosmetic or nutraceutical composition comprising at least one compound derived from tyrosine of general formula 1:

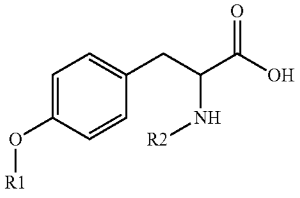

wherein:

R1 is a hydrocarbon chain of 1 to 12 carbon atoms; and

R2 is selected from octanoyl (C8), decanoyl (C10), lauroyl (C12), myristoyl (C14), palmitoyl (C16), stearoyl (C18), biotinoyl, elaidoyl, oleoyl and lipoyl in a physiologically acceptable carrier, wherein the cosmetic or nutraceutical composition is a treatment to improve or beautify the general condition of skin and/or its appendages, and wherein the composition is configured to stimulate skin coloring without UV induction.

3. The method according to claim 1, wherein the group R2 is a-palmitoyl (C16).

4. The method according to claim 1, wherein the tyrosine derivative is the L-isomer.

5. The method according to claim 1, wherein the R1 group is a hydrocarbon chain of 1 to 6 carbon atoms.

6. The method according to claim 1, wherein the R1 group is methyl or ethyl.

7. The treatment method according to claim 1, wherein the tyrosine derivative is N-Palmitoyl-O-methyl-L-Tyrosine, where R1 is methyl, R2 is palmitoyl, the derivative comprising the L-isomer of tyrosine.

8. The method according to claim 1, wherein the method is topical.

9. The method according to claim 1, wherein the method is a preventive or curative treatment.

10. The method according to claim 9, wherein the treatment is further adapted to act on:

hydration; and/or the mechanical properties of the skin; and or oily skins and/or acne prone skins; and/or adipose tissue; and/or signs of skin fatigue; and/or redness and tightness; and/or protection against external aggressions; and/or the scalp; and/or hair, body hair and nails; and/or odors.

11. The method according to claim 10, wherein the method is further selected from a treatment for preventing and/or treating the loss of pigmentation of the skin and its appendages, and/or a treatment for improving the skin phototype of a person with white and/or sensitive skin and/or a self-tanning or tanning-accelerating treatment, and/or a treatment for preventing and/or treating the lack of unification of the complexion.

12. The method according to the claim 1, wherein the method is a treatment of cutaneous white spots and/or canities.

13. The method according to claim 1, wherein the method is a treatment to prepare the skin and its appendages for sun exposure.

14. The method according to claim 1, wherein the cosmetic method is suitable for maintaining and/or improving the elasticity and suppleness of the skin.

15. The composition according to claim 2, wherein the group R2 is palmitoyl (C16).

16. The composition according to claim 2, wherein the tyrosine derivative is the L-isomer.

17. The composition according to claim 2, wherein the R1 group is a hydrocarbon chain of 1 to 6 carbon atoms.

* * * * *